(12) United States Patent
Hunger

(10) Patent No.: US 11,383,061 B2
(45) Date of Patent: Jul. 12, 2022

(54) EXHALATION VALVE FOR A VENTILATOR APPARATUS WITH A VALVE CONFIGURATION FOR REDUCING NOISE EMISSION

(71) Applicant: Hamilton Medical AG, Bonaduz (CH)

(72) Inventor: Jan Hunger, Andeer (CH)

(73) Assignee: HAMILTON MEDICAL AG, Bonaduz (CH)

( * ) Notice: Subject to any disclaimer, the term of this patent is extended or adjusted under 35 U.S.C. 154(b) by 536 days.

(21) Appl. No.: 16/344,657

(22) PCT Filed: Oct. 11, 2017

(86) PCT No.: PCT/EP2017/075952
§ 371 (c)(1),
(2) Date: Apr. 24, 2019

(87) PCT Pub. No.: WO2018/077618
PCT Pub. Date: May 3, 2018

(65) Prior Publication Data
US 2020/0061330 A1 Feb. 27, 2020

(30) Foreign Application Priority Data

Oct. 24, 2016 (DE) ..................... 10 2016 220 812.8

(51) Int. Cl.
*A61M 16/20* (2006.01)
*F16K 15/14* (2006.01)
(Continued)

(52) U.S. Cl.
CPC ........ *A61M 16/206* (2014.02); *A61M 16/205* (2014.02); *F16K 15/144* (2013.01);
(Continued)

(58) Field of Classification Search
CPC ............... F16K 15/144; F16K 15/1441; F16K 15/1401; F16K 15/1402; F16K 15/14;
(Continued)

(56) References Cited

U.S. PATENT DOCUMENTS 2,771,884 A 11/1956 Aghnides
3,251,359 A * 5/1966 Ismach ............. A61M 16/0051
128/205.16

(Continued)

FOREIGN PATENT DOCUMENTS

CN 102343120 A 2/2012
DE 29 22 940 12/1979
(Continued)

OTHER PUBLICATIONS

German Search Report dated Jun. 21, 2017 in DE 10 2016 220 812.8.
(Continued)

*Primary Examiner* — David Colon-Morales
(74) *Attorney, Agent, or Firm* — Tollefson IP

(57) ABSTRACT

An exhalation valve for a ventilator apparatus for at least partial instrumental respiratory assistance of a patient, includes a valve housing with a flow passage which extends along a passage trajectory defining a local axial, radial and circumferential direction and along which respiratory air can flow through the valve housing. The valve housing has a housing-side valve sub-formation with a closed end surface which extends around the passage trajectory and towards which a mating surface of a valve body, movable relative to the valve housing and facing the end surface, can be pretensioned by the pretensioning force of a pretensioning device in such a way that the mating surface, when subjected
(Continued)

to respiratory gas in an exhalation flow direction counter to the pretensioning force of the pretensioning device, is removable.

29 Claims, 6 Drawing Sheets

(51) Int. Cl.
*F16K 47/02* (2006.01)
*A61M 39/22* (2006.01)

(52) U.S. Cl.
CPC ........... *F16K 47/02* (2013.01); *A61M 16/208* (2013.01); *A61M 2039/226* (2013.01); *A61M 2205/42* (2013.01)

(58) Field of Classification Search
CPC ........ F16K 47/02; F16K 47/01; F16K 47/012; A61M 16/208; A61M 16/20; A61M 2039/226; A61M 2205/42; A61M 16/206; A61M 16/201; A61M 16/205
See application file for complete search history.

(56) References Cited

U.S. PATENT DOCUMENTS

| | | | |
|---|---|---|---|
| 3,601,152 A | 8/1971 | Kenworthy | |
| 3,608,574 A * | 9/1971 | Beaussant | A62B 9/027 137/102 |
| 3,726,274 A * | 4/1973 | Bird | A61M 16/201 128/205.24 |
| 3,915,165 A * | 10/1975 | Rambosek | A61D 7/00 128/203.15 |
| 3,933,171 A * | 1/1976 | Hay | A61M 16/208 137/493.7 |
| 4,190,045 A * | 2/1980 | Bartels | A61M 16/20 128/205.24 |
| 4,257,453 A * | 3/1981 | Kohnke | A61M 16/208 137/514.3 |
| 4,406,302 A * | 9/1983 | Olesen | A61M 16/209 137/514.5 |
| 4,454,893 A * | 6/1984 | Orchard | A61M 16/20 128/205.24 |
| 4,611,591 A | 9/1986 | Inui et al. | |
| 4,616,646 A | 10/1986 | Beaussant | |
| 4,694,825 A * | 9/1987 | Slemmer | A61M 16/20 128/205.24 |
| 4,699,137 A * | 10/1987 | Schroeder | A61M 16/206 128/205.24 |
| 4,712,580 A * | 12/1987 | Gilman | A61M 16/20 137/512.15 |
| 4,823,828 A * | 4/1989 | McGinnis | A61M 16/208 128/205.24 |
| 4,964,825 A | 10/1990 | Paccoret et al. | |
| 5,020,532 A * | 6/1991 | Mahoney | A61M 16/20 128/204.18 |
| 5,065,746 A | 11/1991 | Steen | |
| 5,103,854 A * | 4/1992 | Bailey | A61M 16/208 128/205.24 |
| 5,127,400 A * | 7/1992 | DeVries | A61M 16/205 128/205.24 |
| 5,484,270 A | 1/1996 | Adahan | |
| 5,683,232 A | 11/1997 | Adahan | |
| 5,704,348 A * | 1/1998 | Drews | A61M 16/208 128/201.28 |
| 5,927,275 A * | 7/1999 | Loser | A61M 16/205 128/205.24 |
| 6,073,630 A | 6/2000 | Adahan | |
| 6,082,705 A * | 7/2000 | Arvidsson | A61M 16/204 251/129.07 |
| 6,102,038 A | 8/2000 | DeVries | |
| 6,230,708 B1 * | 5/2001 | Radko | A61M 16/208 128/205.24 |
| 6,244,267 B1 * | 6/2001 | Eifrig | A61M 16/204 128/202.22 |
| 8,303,276 B2 * | 11/2012 | Adahan | A61M 16/20 417/534 |
| 9,352,115 B1 * | 5/2016 | DeStefano | A61M 16/06 |
| 10,646,684 B2 * | 5/2020 | Cole | A61M 16/0816 |
| 2010/0095965 A1 * | 4/2010 | Piper | A61M 16/0816 128/205.24 |
| 2011/0016818 A1 | 1/2011 | Trudel | |
| 2011/0168180 A1 * | 7/2011 | Lugtigheid | A61M 16/208 128/205.14 |
| 2014/0150801 A1 * | 6/2014 | Rusher | A63B 21/0088 128/207.16 |
| 2015/0000663 A1 * | 1/2015 | Williams | A61M 16/0066 128/204.19 |
| 2017/0014594 A1 | 1/2017 | Cole | |
| 2020/0179640 A1 * | 6/2020 | Hunger | A61M 16/208 |

FOREIGN PATENT DOCUMENTS

| | | | |
|---|---|---|---|
| DE | 43 31 718 | 3/1995 | |
| DE | 196 11 556 | 5/1997 | |
| DE | 101 14 628 | 9/2002 | |
| DE | 102017208349 A1 * | 11/2018 | ............ F16K 1/523 |
| EP | 0 144 501 | 6/1985 | |
| EP | 0143618 A2 | 6/1985 | |
| EP | 0 158 553 | 10/1985 | |
| GB | 2 027 169 | 2/1980 | |
| JP | 60-132178 A | 7/1985 | |
| WO | 98/41274 | 9/1998 | |
| WO | 99/59517 | 11/1999 | |
| WO | WO-02076544 A1 * | 10/2002 | ............ A61M 16/12 |
| WO | 2009/028938 | 3/2009 | |
| WO | 2015/136407 | 9/2015 | |

OTHER PUBLICATIONS

CN Office Action dated Jun. 9, 2021, for related application.
JP Office Action dated Sep. 13, 2021, for related application.

* cited by examiner

EXHALATION VALVE FOR A VENTILATOR APPARATUS WITH A VALVE CONFIGURATION FOR REDUCING NOISE EMISSION

CROSS-REFERENCE TO RELATED APPLICATIONS

This application is the National Stage of International Application No. PCT/EP2017/075952, filed on Oct. 11, 2017, which claims the benefit of German Application No. 10 2016 220 812.8, filed on Oct. 24, 2016. The contents of both applications are hereby incorporated by reference in their entirety.

The present invention relates to an exhalation valve for a ventilation apparatus for at least partly mechanically assisted ventilation of a patient, encompassing a valve housing having a flow passage which extends along a passage path that defines a local axial, radial, and circumferential direction, and along which respiratory air can flow through the valve housing; the valve housing comprising a housing-mounted valve sub-configuration having an end surface which continuously encircles the passage path and toward which a counterpart surface, facing toward the end surface, of a valve body movable relative to the valve housing is preloaded, by preload force of a preloading device, in such a way that as a result of impingement of a flow of respiratory gas in an exhalation flow direction, the counterpart surface is movable away from the end surface in a lifting direction against the preload force of the preloading device, accompanied by enlargement of an annular gap generatable or present between the end surface and the counterpart surface, so that the flow passage is flowthrough-capable in the exhalation flow direction and so that a flow through the flow passage in a flow direction opposite to the exhalation flow direction is blockable by abutment of the counterpart surface of the valve body against the end surface.

An exhalation valve of this kind is known, for example, from the Applicant's ventilation devices having the "C2" or "C3" product designations. The exhalation valve serves to control respiratory gas transport in a ventilation apparatus.

Ventilation apparatuses usually comprise a respiratory gas conveying pump for conveying fresh respiratory gas to a patient who is to be ventilated. The ventilation apparatus as a rule comprises an inhalation valve that permits conveyance of fresh respiratory gas away from the ventilation apparatus toward the patient but blocks it in the opposite direction, and comprises an exhalation valve that permits a flow of respiratory gas in an exhalation flow direction away from the patient toward the ventilation apparatus but blocks it in the opposite direction.

Known exhalation valves comprise a plate-like valve body that is located oppositely from the end surface of the housing-mounted valve sub-configuration and can also rest thereon in order to block a gas flow in a direction opposite from the exhalation flow direction. That part of the outer surface of the plate-like valve body which is located oppositely from the end surface in a lifting direction, or abuts against it, is then the aforesaid counterpart surface.

The valve body and the housing-mounted valve sub-configuration functionally complement one another to yield a valve configuration that can perform a valve function in the sense of flow control.

In the known exhalation valves, the plate-shaped valve body experiences flow impingement in an exhalation flow direction during an exhalation event, so that the respiratory gas pressure rises on the flow impingement side of the valve body while ambient pressure continues to exist on the negative side of the valve body oppositely from the flow impingement side. When the pressure rise on the flow impingement side overcomes the preload force of the preloading device, the valve body becomes moved away from the end surface so that an annular gap occurring or present between the valve body, or its counterpart surface, and the end surface becomes enlarged. The flow resistance of the exhalation valve in an exhalation flow direction decreases sharply as a result, so that exhausted respiratory gas can flow away from the patient in an exhalation flow direction without a great deal of resistance.

The valve body of the known exhalation valve, constituting a plate-shaped valve body, deflects the respiratory gas flow incident upon it through approximately 90 degrees, so that when the valve body is sufficiently far from the end surface, the respiratory gas flows radially through the above-described annular gap. Periodic eddying and local flow detachments can occur in this context in the region between the end surface and valve body, and can cause pressure fluctuations in the exhalation valve. In some operating states, these pressure fluctuations are undesirably acoustically perceptible outside the exhalation valve and outside the ventilation apparatus. Depending on the periodicity of the pressure fluctuations, they can be manifested as whistling or hissing.

The object of the present invention is therefore to refine the exhalation valve of the species in such a way that it emits less noise during operation as intended, with no limitation of its performance as an exhalation valve.

This object is achieved according to the present invention by an exhalation valve of the kind recited previously in which the valve body comprises a skirt which, when considering the exhalation valve in a reference state not stressed by a respiratory flow as intended, extends in a circumferential direction surrounding the counterpart surface and the end surface, and which in the reference state projects axially beyond the end surface, oppositely to the lifting direction, in a direction away from the counterpart surface, an annular gap space being provided radially between the skirt and an end portion, comprising the end surface, of the valve sub-configuration.

Because the exhalation valve according to the present invention is preferably provided intentionally detachably or removably on a ventilation apparatus, the inhalation valve will be discussed in a reference state in which it is not stressed by a respiratory flow. This corresponds approximately to a reference state in which an exhalation valve removed from a ventilation apparatus is on a shelf or workbench ready for further use.

Thanks to the skirt that surrounds the counterpart surface and the end surface in a reference state, i.e. surrounds them radially externally with reference to a body axis passing centrally through the valve body in a lifting direction, an exhalation flow striking the valve body is no longer only deflected radially outward, but instead is constrainedly deflected at the skirt in a flow direction having a component opposite to the exhalation flow, which must then flow, in the direction opposite to the impinging exhalation flow, through the annular gap space formed between the skirt and the valve sub-configuration.

The result is that because the skirt is provided, the exhalation flow becomes guided along a longer travel path than in the existing art, beyond the end surface past the valve sub-configuration and past the valve body. Whereas in the existing art the exhalation flow flows substantially as an open jet once it has passed the end surface, in the state according to the present invention the exhalation flow is still, even after passing the end surface, physically guided by the skirt and by the valve sub-configuration, both of which delimit the aforesaid annular gap space.

It should be added that what is meant by an aforesaid "local coordinate direction" (axial, radial, circumferential direction) defined by the passage path is that identically named passage-path-related coordinate directions, considered in an absolute coordinate system, can be distinguished depending on the location along the passage path, for example because the passage path has a curved or angled profile.

The annular gap space preferably radially externally surrounds that portion of the flow passage which is located upstream from the counterpart surface with reference to the exhalation flow direction, in which portion the exhalation flow is directed toward the valve body.

Proceeding oppositely to the lifting direction from a portion of the valve body comprising the counterpart surface, the skirt can extend to any distance from the portion, so that regardless of the operating position of the valve body, the annular gap space, although it has different gap space heights to be measured parallel to the lifting direction, can exist over the entire intended movement range of the valve body in a lifting direction. Alternatively, however, the skirt can have a shorter dimension oppositely to the lifting direction than the maximum lifting travel of the valve body, starting from its reference position, in a direction away from the end surface, so that when the valve body exceeds a predetermined threshold lifting travel distance during an exhalation event, the skirt is no longer radially internally opposite any portion of the valve sub-configuration and an annular gap space therefore no longer exists.

As a result of the provision of the skirt, and because of the associated change in the flow conditions at the valve body, the flow conditions achieved in the region of the end surface and counterpart surface during an exhalation event are more stable than at the skirt-less valve body of the existing art. The more-stable flow conditions result in fewer further pressure fluctuations or even none at all, so that the noise emissions associated in the existing art with repeated or periodic eddying and pressure fluctuation are considerably reduced.

The reduction in the noise emissions of the exhalation valve is particularly pronounced in an operationally relevant volumetric flow range of approximately 15 liters per minute.

In principle, the skirt can have at its free longitudinal end, located remotely from the counterpart surface, a smooth rim, for example a rim that is located in a plane orthogonal to the lifting direction.

An even more effective diminution in noise emissions that occur during operation can be achieved by the fact that the magnitude of a spacing, to be measured parallel to the lifting direction, between a skirt rim remote from the counterpart surface and the counterpart surface is different at least circumferentially locally depending on the respective position in a circumferential direction. In this case the skirt projects, along its circumference, to different distances away from a portion of the valve body which comprises the counterpart surface. Preferably the spacing or projection length of the skirt changes periodically along its extent in a circumferential direction around the body axis, parallel to the lifting direction, of the valve body, so that flow conditions which are different but periodically recurring can occur along the circumferential extent of the skirt; this can contribute to an additional stabilization of the exhalation flow in the region between the end surface and counterpart surface during an exhalation event. The skirt rim remote from the counterpart surface therefore preferably exhibits a wave shape proceeding in a circumferential direction. A "wave shape" refers here to any periodic change in the aforementioned spacing or projection depth.

The wave shape can have a straight-line boundary and can be configured, for example, as a sawtooth profile or triangular-wave profile; a triangular profile, having a sequence of equilateral triangles succeeding one another in a circumferential direction, is preferred on the basis of previously obtained test results. Identical equilateral triangles preferably succeed one another in a circumferential direction.

It is likewise conceivable for the side rim, remote from the counterpart surface, to comprise a rectangular wave shape as a side rim having a straight-line boundary.

Alternatively or additionally, the side rim can have a partial-circle wave shape or in general a sinusoidal wave shape, so that in this case the skirt rim is defined by a curvilinear rim line preferably having no corners or kinks.

It is also preferred for the rectangular wave shape and for the partial-circle wave shape, and for the sinusoidal wave shape, of the skirt rim, that the skirt rim be constituted by a sequence of identical rim elements succeeding one another in a circumferential direction.

In order to achieve periodically changing flow conditions that are as uniform as possible along the circumference of the skirt, it is preferred that at least some, preferably all, of the extreme points of the wave crests located farthest from the counterpart surface oppositely to the lifting direction be located on one plane, and/or that at least some, preferably all, of the extreme points of the wave troughs located closest to the counterpart surface oppositely to the lifting direction be located on one plane, in particular on a plane that is orthogonal to the course of the passage path at the penetration point of the plane and/or orthogonal to the lifting direction. This is preferred especially when the inhalation flow direction directly at the valve body is substantially identical to the lifting direction. If the extreme points both of the wave crests and of the wave troughs respectively lie on a plane, there exist two, preferably parallel, extreme-point planes that are arranged at a distance from one another equal to the spacing of the wave amplitude.

Preferably the counterpart surface and/or the end surface is located in one plane. That plane is preferably oriented orthogonally to the lifting direction.

A "plane" is not meant here as an infinitely thin plane in the mathematical sense. The counterpart surface and/or the end surface are instead already to be regarded as "located in a plane" if at least one axial rim of the counterpart surface or of the end surface, preferably both rims adjoining the respective surfaces axially along the lifting direction, are flat. The counterpart surface and/or the end surface can describe, for example, the enveloping surface of a truncated cone.

By means of surfaces, from among the counterpart surface and end surface, located in a plane, outstanding sealing effects can be ensured simultaneously with a centering effect of the end surface and counterpart surface in interaction with one another, with no need to provide an unnecessarily large installation space therefor.

Preferably the counterpart surface and/or the end surface are flat. The exhalation valve can then be configured with particularly short dimensions. A centering effect between the counterpart surface and end surface is then absent, but a centering effect can be brought about by the aforementioned preloading device.

A flat counterpart surface and/or end surface is a special form of a counterpart surface and/or end surface located in a plane. The plane in which the counterpart surface and/or the end surface are located is preferably parallel to the plane on which the farthest and/or closest extreme points respectively of the wave troughs and wave crests of a wave-shaped skirt rim are located.

The end surface can be located or embodied at a longitudinal end of a tubular portion of the flow passage. The tubular portion of the flow passage then constitutes the aforementioned end portion of the valve sub-configuration. Preferably the flow passage is constituted, on the side facing toward the valve body in an exhalation flow direction, by a respiration tube, in particular a straight respiration tube, that can be part of the valve housing. A tube axis of the respiration tube then preferably coincides over the entire tube length, but at least in the region close to the valve body, with a line parallel to the lifting direction. The exhalation flow direction then proceeds along the respiration tube axis. The respiration tube axis is collinear with the above-described valve body axis. The tube axis is part of the passage path.

In the reference state the skirt then surrounds an end region, extending along the passage path (which likewise coincides with the respiration tube axis in the region of the respiration tube when a respiration tube is used) and in a circumferential direction around it, of the tubular portion. That end region of the tubular portion, in particular of the respiration tube, which comprises the end surface thus constitutes, together with the skirt surrounding it, the aforementioned annular gap space. The skirt and the longitudinal end of the tubular portion thus axially overlap along the respiration tube axis or along the passage path.

For improved flow guidance, a radially outer region of the longitudinal end of the tubular portion can be beveled. In this case, because of the bevel at the longitudinal end of the tubular portion, the radial extent of the end face is shorter in a radial direction than the radial dimension of the tubular portion that is assumed to be unbeveled. It is then possible to furnish, between the end surface and the skirt that radially externally surrounds it and has the bevel, an expansion space which acts in a radial direction and into which the exhalation flow, deflected in a radial direction by the valve body, can expand after sliding past the end surface.

To ensure that the skirt can optimally provide its above-described flow guidance effect even in the context of a beveled portion, the skirt extends, at least in the reference state, oppositely to the lifting direction beyond the bevel end located axially farther from the end surface. An annular gap surface can thus exist in a region between the bevel end located remotely from the end surface and the exposed skirt rim. It is also conceivable, however, in the context of the above-described preferred wave-shaped embodiment of the exposed skirt rim, to arrange the wave troughs, i.e. the edge regions located closer to the counterpart surface, less far from the counterpart surface than the bevel end located farther from the end surface. The wave crests can, however, extend oppositely to the lifting direction beyond the relevant bevel end. In this case it is possible to constitute, proceeding from the radial expansion space constituted by the bevel, escape openings that, as a result of the wave shape, can be located periodically in a circumferential direction around the end region of the tubular portion.

In design terms, it has proven to be advantageous in terms of decreasing the operating noise of the exhalation valve if, in the reference state, on the one hand the radial spacing between the bevel end located closer to the end surface and a radially inward-facing wall of the skirt, and on the other hand the overlap depth of the skirt and the tubular portion parallel to the lifting direction, differ by no more than 20%, preferably by no more than 10%, particularly preferably are identical.

For the same reason, it is likewise advantageous in design terms if, in the reference state, on the one hand the radial dimension of the annular gap space and on the other hand the radial thickness of the skirt differ, in an end region of the skirt containing the skirt rim located remotely from the counterpart surface, by no more than 20%, preferably by no more than 10%, particularly preferably are identical. A short exhalation valve can be obtained by the fact that a part of the flow passage is constituted by a respiration tube and by an annular channel surrounding the respiration tube, preferably coaxially, the annular gap between the end surface and counterpart surface being constituted in terms of flow mechanics between the respiration tube and the annular channel in the exhalation flow direction. The short dimension of the exhalation valve along the respiration tube axis is obtained at the cost of a larger diameter because of the annular channel, but the annular channel requires only a slight increase in the diameter of the valve housing in order to furnish an annular channel having the same flow cross section as the respiration tube surrounding the annular channel.

As a very general principle, the valve body can be a valve body of any conformation. The valve body can be, for example, a valve ball. Preferably, however, the valve body is a valve body already used successfully in exhalation valves, having a substantially flat plate portion that comprises the counterpart surface. A valve body of this kind contributes further to a short design for the exhalation valve. Preferably, the plate portion is provided centrally on the valve body.

The preloading device can be constituted by any apparatus that exerts a preload force, e.g. including one or several helical compression springs. A physically short preloading device that at the same time not only preloads the valve body or its plate portion toward the end surface, but can also center with reference thereto, is a diaphragm spring that radially externally surrounds the plate portion and connects the plate portion to a fastening portion, surrounding it at a radial distance, of the valve body.

Particularly preferably, the preloading device not only preloads the counterpart surface toward the end surface, but also preloads the counterpart surface, and/or a valve portion comprising the counterpart surface, into a predetermined idle position in a plane orthogonal to the lifting direction. This can be implemented by a preloading device that is arranged in a circumferential direction around the counterpart surface and acts in different radial directions toward the center of the passage path at the latter's penetration point through a valve body portion comprising the counterpart surface. The aforesaid diaphragm spring, which radially externally surrounds the plate portion or a valve body portion comprising the counterpart surface, can be used as such a preloading device. The preloading device can thereby center the counterpart surface relative to the passage path.

Additionally or alternatively, the preloading device can guide the counterpart surface or a valve body portion comprising the counterpart surface, for example the aforementioned plate portion, in or oppositely to the lifting direction during a lifting and return motion. The guidance need not be an exact guidance in the sense of confinement to a track. It is sufficient in the present case if the preloading device limits a deviation of the motion of the counterpart surface from the lifting direction, so that during operation as intended, the counterpart surface can deviate from an ideal motion path in the lifting direction only by a maximum amount that is determined by the preloading device and cannot be exceeded.

The fastening portion can be embodied for preferably positively engaged connection to the valve housing, in particular to a portion of the valve housing which delimits the annular channel. The fastening portion can then be secured on a housing portion of the valve housing which radially externally surrounds the annular channel, the diaphragm spring can span the radial distance to a respiration tube located radially farther inward, and the plate portion can be located oppositely from an end portion of the respiration tube. To facilitate installation of the valve body, the latter is preferably embodied rotationally symmetrically with reference to a valve body axis passing through the plate portion orthogonally to the plate plane.

The valve body is preferably constituted from an elastomeric material, for example silicone, rubber, and the like.

In the reference state, the counterpart surface can rest on the end surface or can be arranged at a short distance therefrom, "short" to be defined with reference to the operationally maximum stroke length of the counterpart surface in a lifting direction during an exhalation event. A spacing of the counterpart surface from the end surface in the reference state preferably does not exceed 10%, or by preference 5%, of the operationally maximum possible spacing of the counterpart surface from the end surface during an exhalation event.

The valve body is preferably embodied in one piece so that the fastening portion, the diaphragm spring, and the plate portion form one monolithic component. In order to reinforce the plate portion, a reinforcing component, for example a metal disk and/or a ceramic disk, can be provided on it. In order to allow the plate portion to be protected from external influences and stresses, the reinforcing component is preferably exposed in the state mounted on the plate portion, particularly preferably on the side that faces away from the end surface, i.e. is not impinged upon by the exhalation flow.

An actuator, a positioning member of which interacts with the valve body at least in order to displace the counterpart surface oppositely to the lifting direction, can be connected to the valve housing in order to allow the exhalation valve to be controlled, if applicable, independently of the patient's respiratory activity. The positioning member can be a mechanical positioning member, for example a plunger, a control arm, or a connecting member, which interacts with the plate portion, in particular with the reinforcing member thereon, or is in fact mechanically coupled for movement together therewith. In the context of a magnetized reinforcing component, however, the positioning member can also be an armature or armature portion of a selectably energizable electromagnet. For example, an actuator housing or in general an actuator carrier structure can be connected to the valve housing, the positioning member of the actuator being movable relative to the actuator housing or actuator carrier structure in order to interact with the valve body.

The actuator is also to be considered "connected" to the valve housing when the actuator, for example an actuator housing or in general an actuator carrier structure, is fixedly connected to the valve housing by interposition of one or several components.

For closure of the exhalation valve by the actuator, it can be sufficient if the positioning member interacts with the valve body only to displace the counterpart surface oppositely to the lifting direction. This does not necessarily require permanent coupling of the positioning member to the valve body. It can then be sufficient that a plunger is extended toward the valve body, comes into abutting engagement therewith, and pushes it with its counterpart surface against the end surface. The positioning member can be liftable in a lifting direction off the plate portion, in particular off the reinforcing component, in order to enable a lifting motion of the counterpart surface brought about only by the exhalation flow.

The abutting engagement that can be temporarily established between the positioning member and plate portion, in particular with the exposed portion of the reinforcing component, is an embodiment of a couplability of the positioning member of the actuator to the valve body. In order to allow the valve body to be moved both oppositely to the lifting direction and in the lifting direction by the actuator, the latter can be magnetically or mechanically coupled or couplable to the valve body, in particular to the reinforcing component, for example by way of a mechanical latch or a magnetic coupling or coupling capability.

If the mechanical latch is embodied to be capable of being overcome, it can also easily be released again as necessary.

The present invention further relates to a ventilation apparatus for at least partly mechanically assisted ventilation of a patient, which comprises a respiratory gas conveying pump in order to produce a conveyed flow of respiratory gas, which further comprises an inhalation valve, and which comprises an exhalation valve as described above. A housing of the ventilation apparatus can be the component, or one of the components, by means of which the actuator is connected to the valve housing. For example, both the valve housing and an actuator housing can be fixedly connected to the housing of the ventilation apparatus. The actuator housing is then also connected to the valve housing.

Because the refinement of the exhalation valve of the species recited initially is implemented substantially on the valve body in order to achieve the aforementioned object, the present invention also relates to a valve body for an exhalation valve, in particular for an exhalation valve embodied in accordance with the description above. A valve body of this kind encompasses an abutment surface (referred to above as a "counterpart surface") that is embodied for abutment against a valve seat surface (referred to above as an "end surface") and is movable along a motion axis in and oppositely to a lifting direction; the abutment surface enclosing a, preferably right, angle with the motion axis; and the valve body comprising a skirt which surrounds the abutment surface radially externally with reference to the motion axis and which, proceeding from a valve body portion comprising the abutment surface, protrudes from the valve body portion axially with reference to the motion axis and in that context projects axially beyond the abutment surface, in particular projects along its entire circumference around the motion axis.

The valve body portion can be the aforementioned plate portion. The motion axis can be the aforementioned valve body axis of the valve body and/or can coincide in terms of direction with the aforementioned passage path in the region of the abutment surface/counterpart surface.

Aforementioned refinements of the exhalation valve which relate only to the valve body are also advantageous refinements of the valve body according to the present invention, and vice versa. This applies in particular to the wave-shaped embodiment of the exposed skirt rim at that axial longitudinal end of the skirt which is located farther from the abutment surface/counterpart surface. No part of the abutment surface, and also no further abutment surface, is preferably embodied at the longitudinal end of the skirt.

The valve body preferably comprises a preloading device that is connected to, in particular connected in one piece with, the valve body portion comprising the abutment surface/counterpart surface, and that opposes a preload force to a displacement of the valve body portion both along the motion axis and orthogonally thereto. The preloading device is preferably such that the preload force exerted by it on the valve body portion rises, starting from its unstressed idle position, with increasing displacement of the valve body portion.

Also preferably, the valve body comprises a fastening portion with which the valve body is fastenable on a valve housing or in general on a basic valve structure. The fastening portion is preferably embodied in one piece with the valve body portion, particularly preferably also in one piece with the preloading device. The fastening portion advantageously comprises a positive-engagement configuration for fastening the valve body.

The preloading device is preferably embodied as a diaphragm spring. In order to furnish identical preload forces independently of circumferential location, it preferably surrounds the valve body portion completely around the motion axis.

The present invention will be presented in further detail below with reference to the appended drawings, in which.

Figure 1:
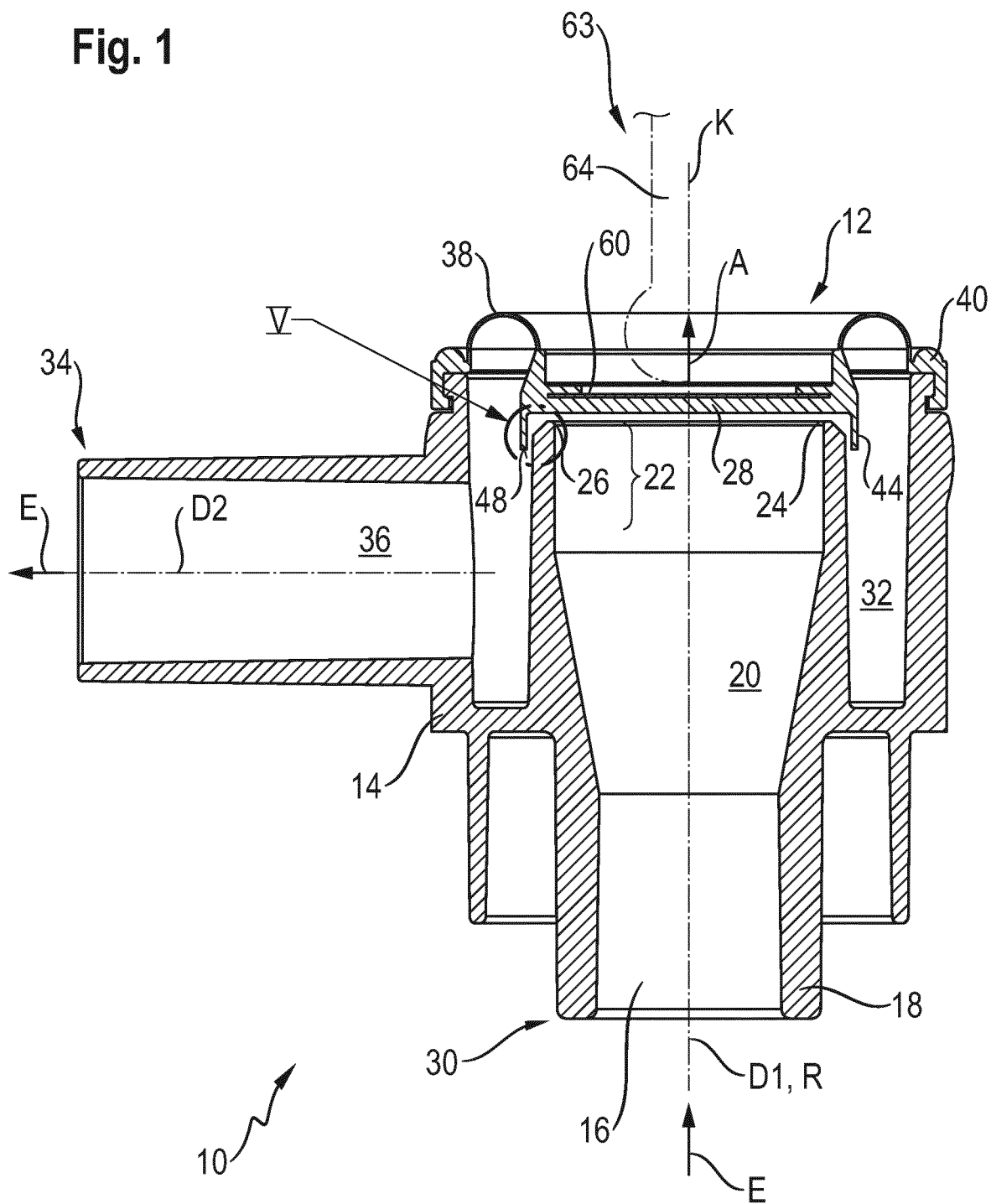
FIG. 1 is a longitudinal section view of an exhalation valve according to the present invention of the present Application.

In FIG. 1, an embodiment according to the present invention of an exhalation valve of the present Application is labeled in general with the number 10 and depicted in longitudinal section. The section plane contains passage path D, which in the embodiment shown comprises two portions, namely portion D1 upstream of a valve body 12, and portion D2 downstream from valve body 12, in exhalation flow direction E.

Valve body 12 is retained on a valve housing 14 that is preferably manufactured integrally, for example using the injection molding method.

A flow passage 16, which extends along passage path portions D1 and D2, is embodied in the valve housing or housing 14.

Housing 14 comprises a respiration tube 18, embodied integrally thereon, which proceeds in a straight line along passage path portion D1, widening locally in exhalation flow direction E toward valve body 12. Passage path portion D1 therefore coincides with tube axis R of respiration tube 18. Respiration tube 18 thus constitutes an upstream flow passage portion 20 of flow passage 16. Embodied at an end portion 22 of respiration tube 18 located closest to valve body 12 is an end surface 24 at the end of respiration tube 18 encircling flow passage 16 in that region, which surface is located oppositely from a counterpart surface 26 of a plate-like portion 28, embodied to be substantially flat, of valve body 12.

Figure 2:
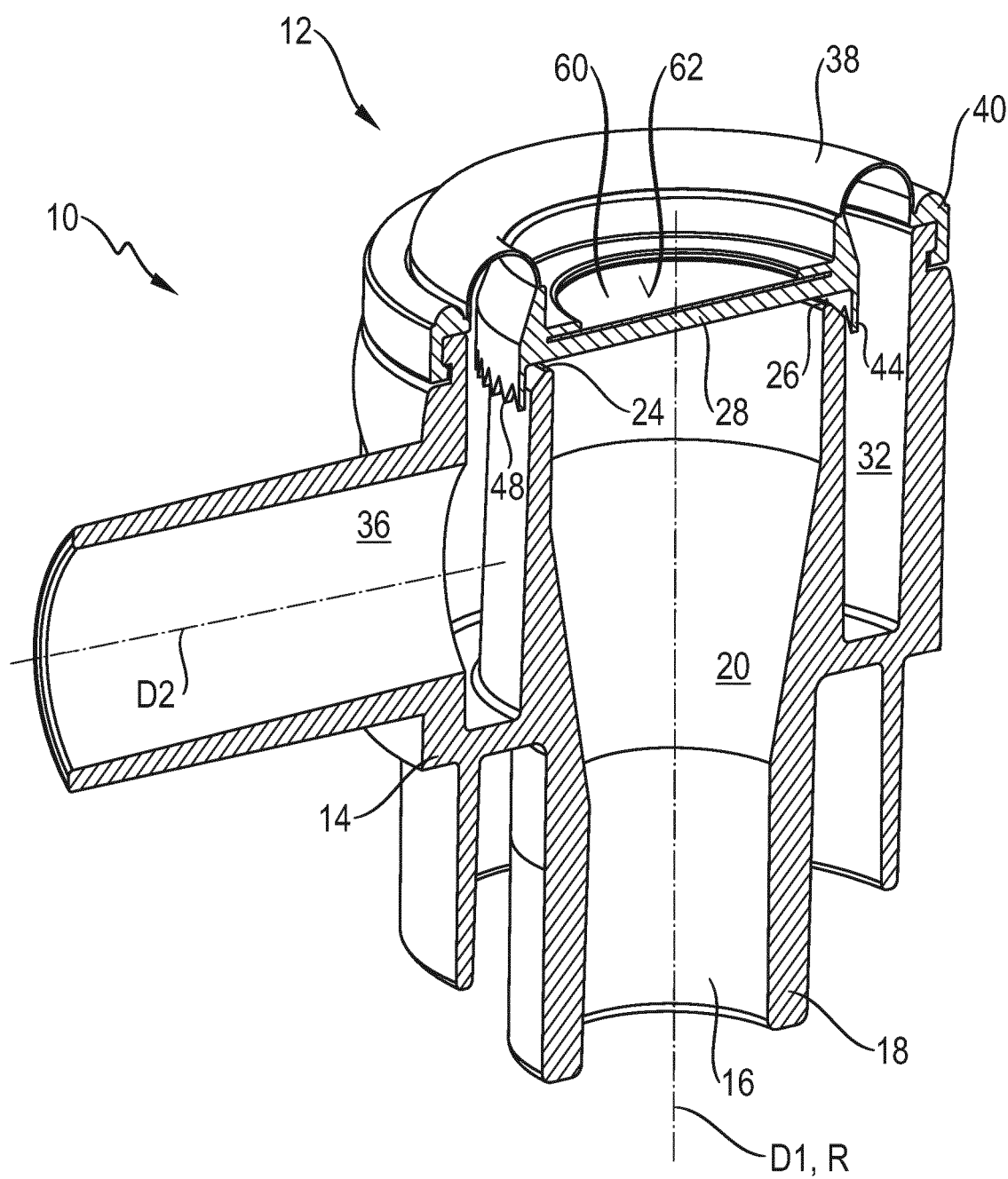
FIG. 2 is a longitudinally section perspective view of the exhalation valve of FIG. 1.
Figure 5:
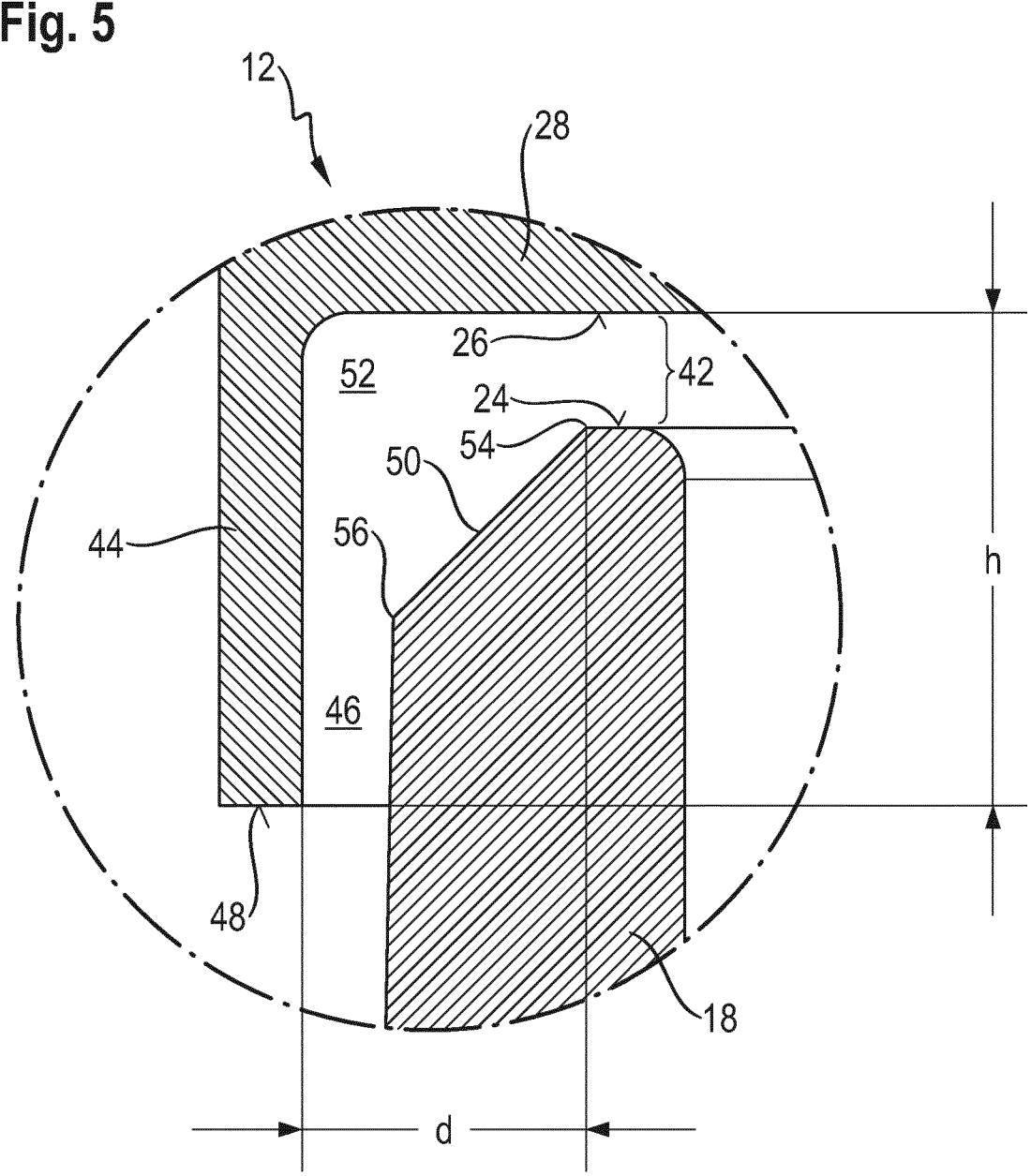
FIG. 5 is a detail view of portion V of FIG. 1.

In the reference state depicted in the Figures, counterpart surface 26 is located at a small gap distance from end surface 24. As soon as a patient connected to proximal end 30 of exhalation valve 10 inhales, however, the pressure difference thereby produced at valve body 12 would cause the latter to move toward end surface 24 until counterpart surface 26 sits on end surface 24, so that flow passage 16 is then blocked for flow through it in a direction opposite to exhalation direction E. Alternatively to what is depicted in FIGS. 1, 2, and 5, valve body 12 can already, in the reference state unstressed by a respiratory gas flow of a patient, sit with counterpart surface 26 on end surface 24.

The downstream part of flow passage 16, i.e. the portion located behind valve body 12 in terms of flow mechanics in exhalation flow direction E, is constituted from two sub-portions: A first downstream portion 32, located closer to valve body 12, of flow passage 16 is embodied as an annular channel concentrically with end portion 22 of respiration tube 18 and thus concentrically with upstream portion 20 of flow passage 16. The annular channel of portion 32 surrounds the upstream portion of flow passage 16 radially externally with reference to passage path portion D1, which is the passage path portion both for upstream portion 20 and for downstream portion 32, located closer to valve body 12, of flow passage 16.

Flow passage 16 encompasses a stub conduit 36, leading toward distal end 34 of exhalation valve 10, which emerges orthogonally from annular channel 32 or from portion 32 of flow passage 16 which forms the annular channel and is located closer to valve body 12. Portions D1 and D2 of the passage path are arranged orthogonally to one another in FIGS. 1 and 2, and intersect if portion D2 is notionally prolonged. This is merely a preferred arrangement, however. Depending on the space circumstances available in a ventilation apparatus that receives exhalation valve 10, portions D1 and D2 can be askew, i.e. can not intersect one another, and/or can also enclose between one another angles other than the right angle shown in FIG. 1.

Plate-like portion 28 of valve body 12, which comprises counterpart surface 26, is embodied to be substantially flat and oriented orthogonally to passage path portion D1. Passage path portion D1 furthermore forms, or coincides with, a body axis K that passes centrally through valve body 12 substantially as a rotational symmetry axis.

Plate-like portion 28 having counterpart surface 26 embodied thereon is connected, via a diaphragm spring 38 proceeding completely around body axis K or flow passage portion D1, to a fastening portion 40 embodied radially outside plate portion 28.

Fastening portion 40 is connected in positively engaging fashion, in a manner known per se, to a portion of valve housing 14. Valve body 12 in its entirety is retained on valve housing 14 by fastening portion 40. Diaphragm spring 38 centers plate-like portion 28 relative to respiration tube 18 and preloads plate-like portion 28 toward end surface 24, or presents a resistance that opposes lifting of plate-like portion 28, or of counterpart surface 26 provided thereon, away from end surface 24. Preferably, the farther counterpart surface 26 is from end surface 24 along first flow passage portion D1 in lifting direction A, the greater the resistance.

In the exemplifying embodiment described here, lifting direction A proceeds along first portion D1 of the passage path.

During an exhalation event of a patient connected to proximal end 30 of exhalation valve 10, the pressure in upstream portion 20 of flow passage 16 becomes elevated while ambient pressure is constantly present on that side of valve body 12 which faces away from respiration tube 18. As a result of the pressure elevation on that side of plate-like portion 28 which is impinged upon by pressure, there acts on plate-like portion 28 a pressure force, acting in lifting direction A, which overcomes the elastic force of diaphragm spring 38 as the pressure difference increases, so that plate-like portion 28, and with it counterpart surface 26, become displaced in lifting direction A away from end surface 24. An annular gap 42 (see FIG. 5), formed or existing between end surface 24 and counterpart surface 26, thereby becomes enlarged. The flow resistance in exhalation direction E between end surface 24 and counterpart surface 26 decreases as a result, so that an exhalation flow from proximal end 30 toward distal end 34 of exhalation valve 10 is possible with almost no impediment.

The exhalation flow proceeding in exhalation flow direction E is constrainedly deflected at plate-like portion 28 of valve body 12 so that it flows in a radial direction, with reference to passage path portion D1, away from passage path portion D1 through annular gap 42.

In order to stabilize this exhalation flow in that portion of flow passage 16 which is located directly downstream from annular gap 42 between end surface 24 and counterpart surface 26, valve body 12 comprises a skirt 44 that prevents the exhalation flow from flowing out exclusively radially after passing through annular gap 42, and deflects the exhalation flow again, this time in a flow direction having a directional component opposite to the exhalation flow direction directly upstream from valve body 12.

Skirt 44 proceeds in a circumferential direction completely around body axis K of valve body 12 and surrounds both counterpart surface 26 and end surface 24. For that purpose, skirt 44 projects from plate-like portion 28 having counterpart surface 26, oppositely to lifting direction A, sufficiently far that it not only protrudes beyond end surface 24 oppositely to lifting direction A but completely radially externally surrounds an axial end portion, comprising end surface 24, of respiration tube 18. An annular gap space 46 (see FIG. 5), which allows exhalation flow to flow off even when counterpart surface 26 is only slightly lifted off from end surface 24, is constituted between respiration tube 18 and skirt 44.

The result of the skirt which completely surrounds annular gap 42 at least when exhalation valve 10 is in the reference position is to achieve a stabilization of the exhalation flow in the region of the valve passthrough, which has considerably less tendency toward eddying and flow detachment compared with a similar valve body 12 having no skirt as has hitherto been used in the existing art, thereby enabling an exhalation flow accompanied by considerably less noise. Experiments have shown that an exhalation valve according to the present invention exhibits substantially reduced noise emission, compared with exhalation valves of the existing art, especially in a volumetric flow range of approximately 15 liters per minute.

Skirt 44 can extend, oppositely to lifting direction A, sufficiently far from plate-like portion 28 and counterpart surface 26 embodied thereon, that an annular gap space 46 remains between skirt 44 and the outer side of respiration tube 18, until the lifting of counterpart surface 26 away from end surface 24 has exceeded a predetermined magnitude.

Figure 3:
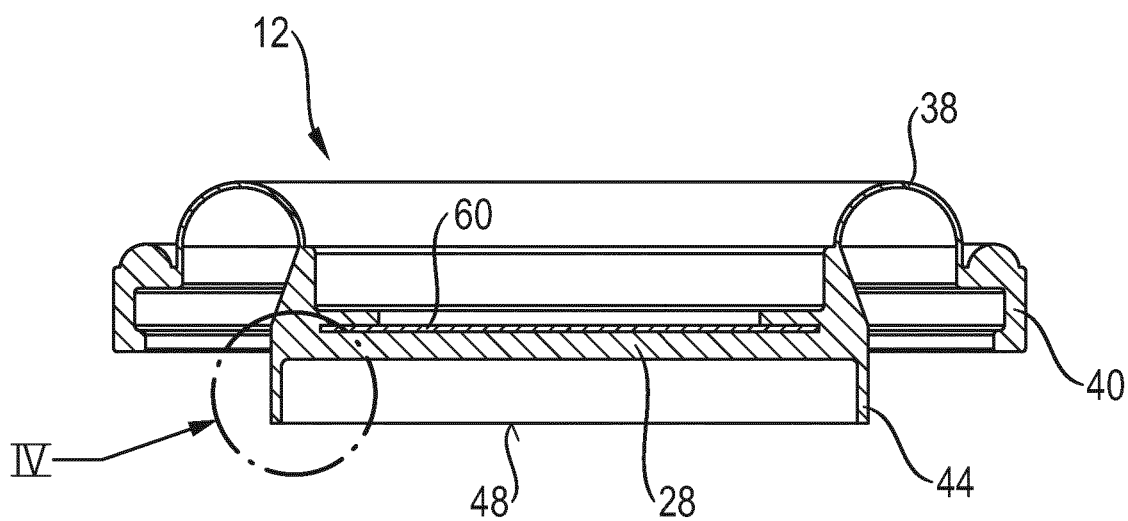
FIG. 3 is a longitudinal section view through the valve body of the exhalation valve of FIGS. 1 and 2, which is also of itself a valve body according to the present invention.
Figure 6:
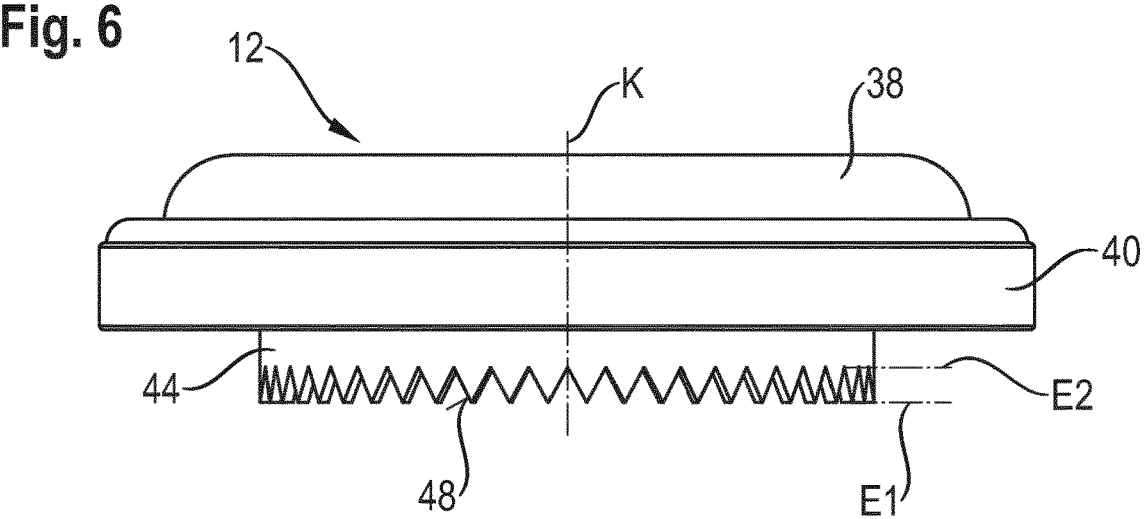
FIG. 6 is an elevation view of the valve body of the exhalation valve of FIG. 2.
Figure 7:
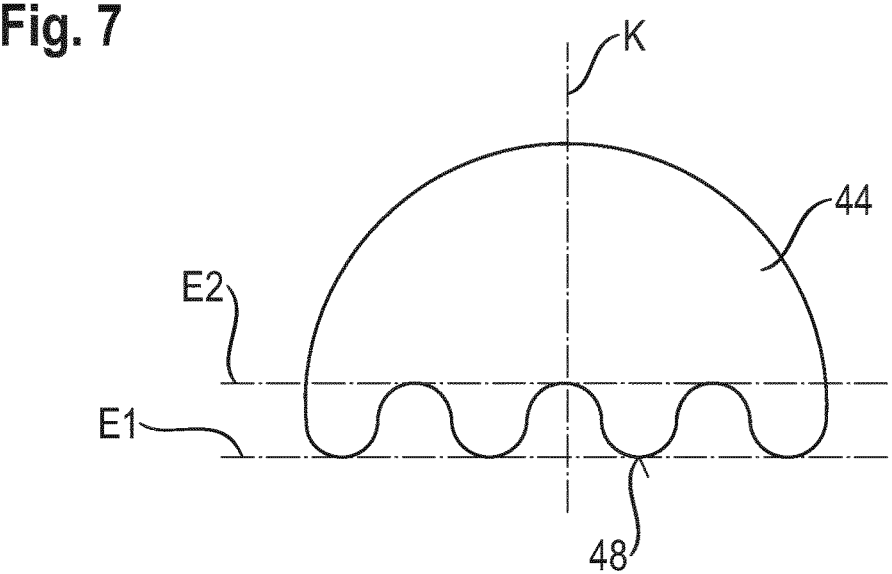
FIG. 7 shows a first alternative configuration of the exposed skirt rim.
Figure 8:
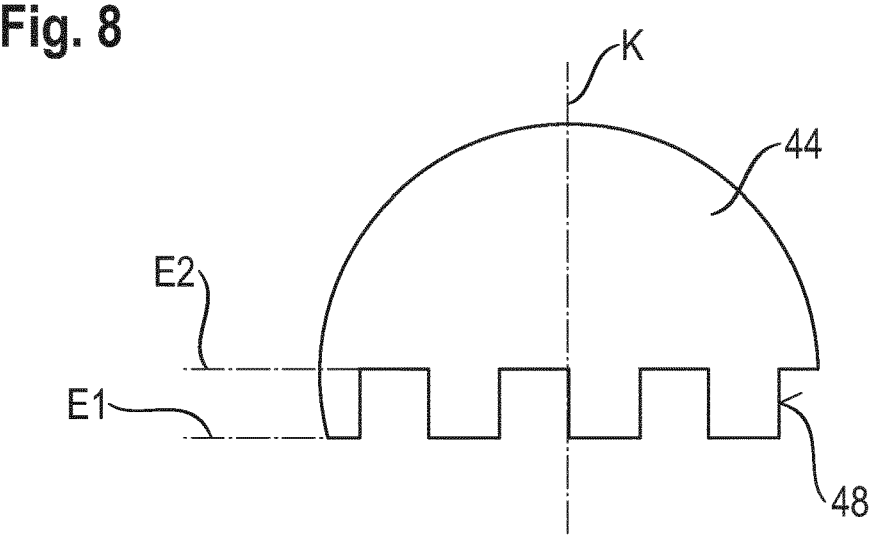
FIG. 8 shows second alternative configuration of the exposed skirt rim.
Figure 9:
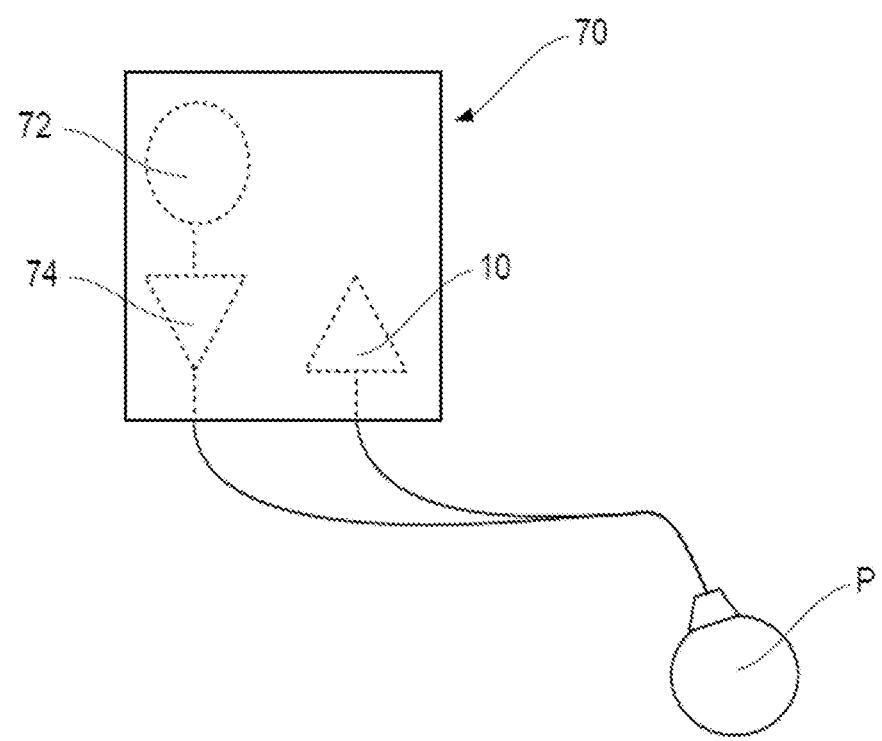
FIG. 9 is a block diagram of a ventilation apparatus having the exhalation valve of the present invention.

As shown in FIG. 1, exposed rim 48 of skirt 44 can be a smooth rim that proceeds along a circular track around body axis K of valve body 12. Exposed rim 48 of skirt 44 can also, however, as shown in FIGS. 2, 3, and 6, have a wave shape, for example a triangular wave conformation having equilateral triangles of equal size succeeding one another in a circumferential direction. Alternatively, as depicted in FIG. 7, rim 48 of skirt 44 can be configured in partially-circular or sinusoidal form or, as shown in FIG. 8, can be configured as a rectangular wave shape. As shown in FIG. 5, respiration tube 18 can be equipped, radially outside end surface 24, with a bevel 50. Bevel 50 preferably proceeds completely around tube axis R of respiration tube 18 and constitutes, in interaction with plate-like portion 28 and skirt 44 projecting therefrom oppositely to lifting direction A, a radially externally acting expansion space 52 (see FIG. 5) into which the exhalation flow flowing radially through annular gap 42 between end surface 24 and counterpart surface 26 can expand.

As shown in FIG. 5, protrusion length h over which skirt 44 projects, oppositely to lifting direction A, from plate-like portion 28 of valve body 12 is greater than radial spacing d between that end 54 of bevel 50 which is closer to end surface 24 and a radially inward-facing wall of skirt 44.

As also shown in FIG. 5, skirt 44 extends oppositely to lifting direction A not only beyond end surface 24 but also beyond that end 56 of bevel 50 which is located farther from end surface 24.

In the context of a wave-shaped embodiment of rim 48 of skirt 44, protrusion length h is to be determined out to an extreme point located farthest from counterpart surface 26, i.e. ignoring the wave troughs.

As is evident from FIGS. 6, 7, and 8, the extreme points of the wave crests located farthest from counterpart surface 26 lie on a first plane E1 orthogonal to body axis K of valve body 12, and the extreme points of the wave troughs located closest to counterpart surface 26 lie on a second plane E2 parallel to the first. Planes E1 and E2 each proceed orthogonally to body axis K of valve body 12.

On its side facing away from respiration tube 18, plate-like portion 28 of valve body 12 preferably comprises a reinforcing disk 60 that stabilizes the shape of plate-like portion 28. The remainder of valve body 12, with the exception of reinforcing disk 60, is preferably constituted integrally from a flexible elastomer, for example silicone, rubber, or natural rubber.

Reinforcing disk 60 not only provides dimensional stabilization of plate-like portion 28 but also forms, with its stable and hard externally exposed surface 62 (see FIG. 2), an engagement surface for an actuator 63 for forced displacement of plate-like portion 28 (and, with it, counterpart surface 26) toward end surface 24. In the interest of clarity, only half an actuator plunger 64 is depicted with dashed lines and indicated in FIG. 1.

Actuator 64 can be brought into abutting engagement with reinforcing disk 60 by being lowered toward it. Once the abutting engagement is established, the entire plate-like portion 28, together with the reinforcing disk, can be moved toward end portion 22 of respiration tube 18 by lowering actuator plunger 64 farther. Plunger 64 can be lifted away from reinforcing disk 60 by being pulled back in lifting direction A. Plunger 64 can be electromagnetically driven to move. It can likewise be driven by an electric-motor drive system, by means of a linkage, to move along body axis K.

Figure 4:
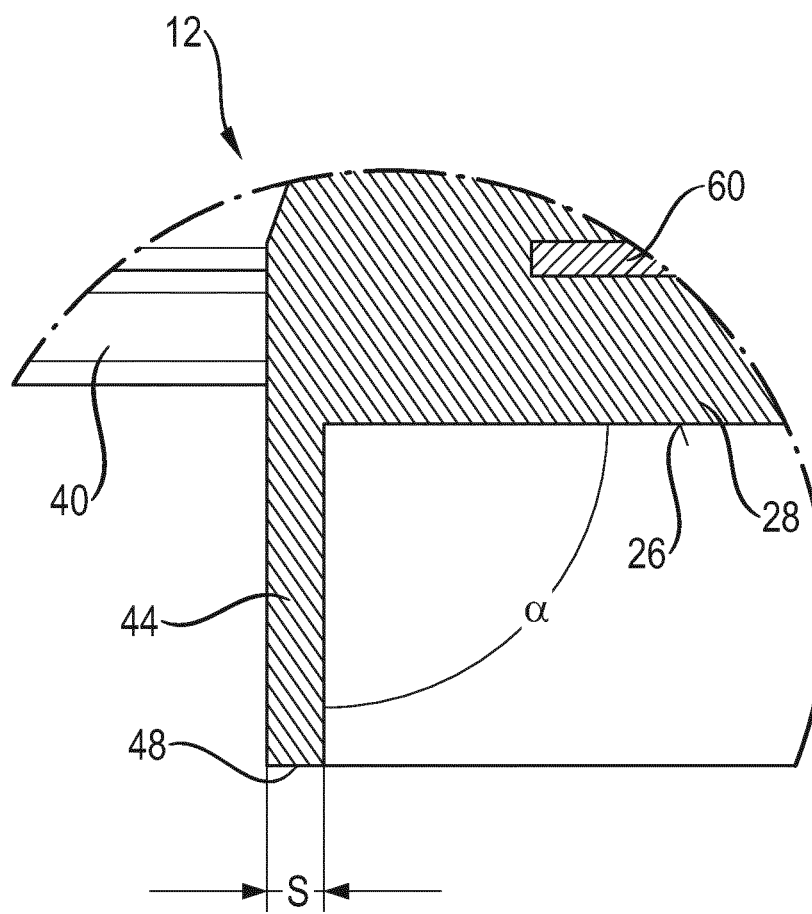
FIG. 4 is a detail view of portion IV of FIG. 3.

FIG. 4 is an enlarged depiction of a detail of valve body 12 of FIG. 3.

In the section plane that encloses body axis K of valve body 12, skirt 44 preferably encloses with the plane of the preferably flat counterpart surface 26 an angle α that is 90 degrees or slightly more than 90 degrees. Angle α is preferably in a range from 90 to 95 degrees, particularly preferably up to 92.5 degrees.

Radial thickness s of skirt 44 is preferably substantially constant along its protrusion length h, with the exception of an unavoidable transition curvature at the transition to plate-like portion 28. It is preferably no more than 10% greater or less than the radial extent of annular gap space 46 between the radially outward-facing surface of respiration tube 18 and the radially inward-facing wall surface of skirt 44.

With the exhalation valve described here it is possible to considerably decrease the noise produced in the context of flow during an exhalation event, with no increase in flow resistance. It is likewise possible, with the exhalation valve that has been presented above, to reliably prevent flow through valve housing 14 in a flow direction opposite to exhalation flow direction E.

FGG. 9 shows a ventilation apparatus 70 including a respiratory gas pump 72, conveying respiratory gas through an inspiratory gas via an inspiratory valve 74 to a patient P. From the patient P expiratory gas is exhaled through expiratory gas expiratory valve 10, as shown in detail in the already existing drawings and described above.

The invention claimed is:

1. An exhalation valve for a ventilation apparatus for at least partly mechanically assisted ventilation of a patient, comprising:
a valve housing having a flow passage which extends along a passage path that defines a local axial, radial, and circumferential direction, and along which respiratory air can flow through the valve housing, the valve housing comprising a housing-mounted valve sub-configuration having an end surface which continuously encircles the passage path; and
a counterpart surface, facing toward the end surface, of a valve body movable relative to the valve housing being preloaded by a preloading device in such a way that as a result of impingement of a flow of respiratory gas in an exhalation flow direction, the counterpart surface is movable away from the end surface in a lifting direction against a preload force of the preloading device, accompanied by enlargement of an annular gap generatable or present between the end surface and the counterpart surface, so that the flow passage is flow-through-capable in the exhalation flow direction and so that a flow through the flow passage in a flow direction opposite to the exhalation flow direction is blockable by abutment of the counterpart surface of the valve body against the end surface;
wherein the valve body comprises a skirt which, when considering the exhalation valve in a reference state not stressed by a respiratory flow as intended, extends in a circumferential direction surrounding the counterpart surface and the end surface, and which in the reference state projects axially beyond the end surface, oppositely to the lifting direction, in a direction away from the counterpart surface, an annular gap space being provided radially between the skirt and an end portion, facing toward the end surface, of the valve sub-configuration;
wherein a magnitude of a spacing, to be measured parallel to the lifting direction, between a skirt rim remote from the counterpart surface and the counterpart surface is different at least circumferentially locally depending on the respective position in a circumferential direction.

2. The exhalation valve according to claim 1, wherein the skirt rim remote from the counterpart surface exhibits a wave shape proceeding in a circumferential direction.

3. The exhalation valve according to claim 2, wherein the wave shape has a triangular and/or rectangular and/or partial-circle wave shape and/or a sinusoidal wave shape.

4. The exhalation valve according to claim 2, wherein at least some of the extreme points of the wave crests located farthest from the counterpart surface oppositely to the lifting direction, and/or at least some of the extreme points of the wave troughs located closest to the counterpart surface oppositely to the lifting direction, are located on one plane.

5. The exhalation valve according to claim 1, wherein the counterpart surface and/or the end surface is/are located in one plane.

6. The exhalation valve according to claim 1, wherein the end surface is located at a longitudinal end of a tubular portion of the flow passage constituting the end portion of the valve sub-configuration; the skirt surrounding, in the reference state, an end region, extending along the passage path and in a circumferential direction around it, of the tubular portion.

7. The exhalation valve according to claim 6, wherein a radially outer region of the longitudinal end of the tubular portion is beveled, the skirt extending, in the reference state, oppositely to the lifting direction beyond the bevel end located axially farther from the end surface.

8. The exhalation valve according to claim 7, wherein in the reference state, the radial spacing between the bevel end located closer to the end surface and a radially inward-facing wall of the skirt, and the overlap depth of the skirt and the tubular portion parallel to the lifting direction, differ by no more than 20%.

9. The exhalation valve according to claim 1, wherein in the reference state, the radial dimension of the annular gap space and the radial thickness of the skirt differ, in an end region of the skirt containing the skirt rim located remotely from the counterpart surface, by no more than 20%.

10. The exhalation valve according to claim 1, wherein a part of the flow passage is constituted by a respiration tube and by an annular channel surrounding the respiration tube, the annular gap between the end surface and counterpart surface being constituted in terms of flow mechanics between the respiration tube and the annular channel in the exhalation flow direction.

11. The exhalation valve according to claim 1, wherein the valve body comprises a substantially flat plate portion which comprises the counterpart surface and which connects to a fastening portion radially externally surrounding the plate portion.

12. The exhalation valve according to claim 11, wherein the plate portion is reinforced by a reinforcing component comprising a metal disk and/or a ceramic disk, the reinforcing component being exposed at least in portions on that side of the plate portion which faces away from the end surface.

13. The exhalation valve according to claim 1, wherein the preloading device preloads the counterpart surface, in a plane orthogonal to the lifting direction, into a predetermined idle position, in particular centers it relative to the passage path in the region of the counterpart surface, and/or guides it during a lifting and return motion respectively in and oppositely to the lifting direction.

14. The exhalation valve according to claim 1, wherein an actuator, a positioning member of which interacts with the valve body at least in order to displace the counterpart surface oppositely to the lifting direction, is connected to the valve housing.

15. The exhalation valve according to claim 14, wherein the positioning member of the actuator is coupled or couplable to the valve body for displacement of the counterpart surface both in and oppositely to the lifting direction.

16. The ventilation apparatus for at least partly mechanically assisted ventilation of the patient of claim 1, comprising:
a respiratory gas conveying pump,
the exhalation valve according to claim 1, and
an inhalation valve.

17. The valve body for the exhalation valve of claim 1, said valve body encompassing an abutment surface of the counterpart surface that is embodied for abutment against a valve seat surface of the end surface and is movable along a motion axis in and oppositely to the lifting direction;
the abutment surface enclosing an angle with the motion axis;
the valve body comprising the skirt which surrounds the abutment surface radially externally with reference to the motion axis and which, proceeding from a valve body portion comprising the abutment surface, protrudes from the valve body portion axially with reference to the motion axis and in that context projects axially beyond the abutment surface.

18. The exhalation valve according to claim 2, wherein all of the extreme points of the wave crests located farthest from the counterpart surface oppositely to the lifting direction, and/or all of the extreme points of the wave troughs located closest to the counterpart surface oppositely to the lifting direction, are located on one plane.

19. The exhalation valve according to claim 1, wherein the counterpart surface and/or the end surface is/are flat.

20. The exhalation valve according to claim 2, wherein at least some of the extreme points of the wave crests located farthest from the counterpart surface oppositely to the lifting direction, and/or at least some of the extreme points of the wave troughs located closest to the counterpart surface oppositely to the lifting direction, are located on a plane that is orthogonal to the course of the passage path at the penetration point of the plane and/or orthogonal to the lifting direction.

21. The exhalation valve according to claim 7, wherein in the reference state, the radial spacing between the bevel end located closer to the end surface and a radially inward-facing wall of the skirt, and the overlap depth of the skirt and the tubular portion parallel to the lifting direction, differ by no more than 10%.

22. The exhalation valve according to claim 1, wherein in the reference state, the radial dimension of the annular gap space and the radial thickness of the skirt differ, in an end region of the skirt containing the skirt rim located remotely from the counterpart surface, by no more than 10%.

23. The exhalation valve according to claim 1, wherein a part of the flow passage is constituted by a respiration tube and by an annular channel surrounding the respiration tube coaxially, the annular gap between the end surface and counterpart surface being constituted in terms of flow mechanics between the respiration tube and the annular channel in the exhalation flow direction.

24. The exhalation valve according to claim 1, wherein the valve body comprises a substantially flat plate portion which comprises the counterpart surface and which connects, by means of a diaphragm spring constituting the preloading device, to a fastening portion radially externally surrounding the plate portion.

25. The exhalation valve according to claim 7, wherein in the reference state, the radial spacing between the bevel end located closer to the end surface and a radially inward-facing wall of the skirt, and the overlap depth of the skirt and the tubular portion parallel to the lifting direction, are identical.

26. The exhalation valve according to claim 1, wherein in the reference state, the radial dimension of the annular gap space and the radial thickness of the skirt are identical in an end region of the skirt containing the skirt rim located remotely from the counterpart surface.

27. The valve body for the exhalation valve of claim 1, encompassing an abutment surface of the counterpart surface that is embodied for abutment against a valve seat surface of the end surface and is movable along a motion axis in and oppositely to the lifting direction; the abutment surface enclosing a right angle with the motion axis; the valve body comprising the skirt which surrounds the abutment surface radially externally with reference to the motion axis and which, proceeding from a valve body portion comprising the abutment surface, protrudes from the valve body portion axially with reference to the motion axis and in that context projects axially beyond the abutment surface.

28. An exhalation valve for a ventilation apparatus for at least partly mechanically assisted ventilation of a patient, comprising:
a valve housing having a flow passage which extends along a passage path that defines a local axial, radial, and circumferential direction, and along which respiratory air can flow through the valve housing, the valve housing comprising a housing-mounted valve sub-configuration having an end surface which continuously encircles the passage path; and
a counterpart surface, facing toward the end surface, of a valve body movable relative to the valve housing being preloaded by a preloading device in such a way that as a result of impingement of a flow of respiratory gas in an exhalation flow direction, the counterpart surface is movable away from the end surface in a lifting direction against a preload force of the preloading device, accompanied by enlargement of an annular gap generatable or present between the end surface and the counterpart surface, so that the flow passage is flow-through-capable in the exhalation flow direction and so that a flow through the flow passage in a flow direction opposite to the exhalation flow direction is blockable by abutment of the counterpart surface of the valve body against the end surface;
wherein the valve body comprises a skirt which, when considering the exhalation valve in a reference state not stressed by a respiratory flow as intended, extends in a circumferential direction surrounding the counterpart surface and the end surface, and which in the reference state projects axially beyond the end surface, oppositely to the lifting direction, in a direction away from the counterpart surface, an annular gap space being provided radially between the skirt and an end portion, facing toward the end surface, of the valve sub-configuration; and
wherein in the reference state, the radial dimension of the annular gap space and the radial thickness of the skirt differ, in an end region of the skirt containing a skirt rim located remotely from the counterpart surface, by no more than 20%.

29. An exhalation valve for a ventilation apparatus for at least partly mechanically assisted ventilation of a patient, comprising:
- a valve housing having a flow passage which extends along a passage path that defines a local axial, radial, and circumferential direction, and along which respiratory air can flow through the valve housing, the valve housing comprising a housing-mounted valve sub-configuration having an end surface which continuously encircles the passage path; and
- a counterpart surface, facing toward the end surface, of a valve body movable relative to the valve housing being preloaded by a preloading device in such a way that as a result of impingement of a flow of respiratory gas in an exhalation flow direction, the counterpart surface is movable away from the end surface in a lifting direction against a preload force of the preloading device, accompanied by enlargement of an annular gap generatable or present between the end surface and the counterpart surface, so that the flow passage is flow-through-capable in the exhalation flow direction and so that a flow through the flow passage in a flow direction opposite to the exhalation flow direction is blockable by abutment of the counterpart surface of the valve body against the end surface;
- wherein the valve body comprises a skirt which, when considering the exhalation valve in a reference state not stressed by a respiratory flow as intended, extends in a circumferential direction surrounding the counterpart surface and the end surface, and which in the reference state projects axially beyond the end surface, oppositely to the lifting direction, in a direction away from the counterpart surface, an annular gap space being provided radially between the skirt and an end portion, facing toward the end surface, of the valve sub-configuration;
- wherein the valve body comprises a substantially flat plate portion which comprises the counterpart surface and which connects to a fastening portion radially externally surrounding the plate portion; and
- wherein the plate portion is reinforced by a reinforcing component comprising a metal disk and/or a ceramic disk, the reinforcing component being exposed at least in portions on that side of the plate portion which faces away from the end surface.

* * * * *